(12) United States Patent
Redoules et al.

(10) Patent No.: US 6,818,657 B1
(45) Date of Patent: Nov. 16, 2004

(54) BIOPRECURSORS OF A RETINOIC DERIVATIVE AND PHARMACEUTICAL AND/OR COSMETIC COMPOSITIONS

(75) Inventors: Daniel Redoules, Toulouse (FR); Roger Tarroux, Toulouse (FR); Didier Fournier, Castanet Tolosan (FR); Jean-Jacques Perie, Castanet Tolosan (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 0 days.

(21) Appl. No.: 09/937,673

(22) PCT Filed: Mar. 31, 2000

(86) PCT No.: PCT/FR00/00822
§ 371 (c)(1),
(2), (4) Date: Sep. 28, 2001

(87) PCT Pub. No.: WO00/58325
PCT Pub. Date: Oct. 5, 2000

(30) Foreign Application Priority Data

Mar. 31, 1999 (FR) .......................................... 99 04032

(51) Int. Cl.$^7$ ...................... C08B 11/00; C07H 15/207; A61K 7/48
(52) U.S. Cl. .................. 514/326; 514/549; 514/255.05; 514/859; 536/18.2; 536/18.1; 536/119; 536/4.1; 536/124; 424/450; 549/417; 510/320; 546/121; 546/153

(58) Field of Search ................. 536/18.2, 18.1, 536/119, 4.1, 124; 424/450; 549/417; 514/326, 549, 255.05, 859; 510/320; 546/121, 153

(56) References Cited

U.S. PATENT DOCUMENTS

| | | | | |
|---|---|---|---|---|
| 4,565,863 A | * | 1/1986 | Bollag et al. ............... 536/18.2 |
| 5,037,655 A | * | 8/1991 | Giovanoni ................... 424/427 |
| 5,126,500 A | * | 6/1992 | von Deessen et al. ....... 536/4.1 |
| 5,621,002 A | * | 4/1997 | Bosslet et al. .............. 514/451 |
| 5,663,377 A | * | 9/1997 | Curley, Jr. et al. .......... 549/417 |
| 5,955,100 A | * | 9/1999 | Bosslet et al. .............. 424/450 |

* cited by examiner

*Primary Examiner*—James O. Wilson
*Assistant Examiner*—Devesh Khare
(74) *Attorney, Agent, or Firm*—The Firm of Hueschen and Sage

(57) ABSTRACT

The present invention relates to a ternary glucosyl complex which is a bioprecursor of at least one retinoic active ingredient for percutaneous application, having formula (I), wherein E represents a linear hydrocarbon spacer group that is branched or cyclized and has an aliphatic or aromatic content capable of containing one or several heteroatoms of oxygen and carrying one or several carbonyl groups; A represents a radical of a molecule of said retinoic active ingredient linked to the spacer group by a carboxylate function and n=1 or 2.

16 Claims, No Drawings

BIOPRECURSORS OF A RETINOIC DERIVATIVE AND PHARMACEUTICAL AND/OR COSMETIC COMPOSITIONS

The present invention relates to a cosmetic or pharmaceutical composition for application to the skin, containing a compound capable of releasing two active substances by action of two enzymatic activities, the activities of glucocerebrosidase and esterase, starting with a glucoconjugate.

It has been confirmed after overexpression of cutaneous β-glucocerebrosidase that this enzyme is indeed capable of recognizing and hydrolyzing such glucoconjugates, thus allowing a slow release of the active substance, without an accumulation effect.

The bioprecursor strategy has been used previously for the release of active agents in two previous cases:

release of retinol from its ester with palmitic acid under the action of the esterase activity of the skin (J. Boenlein, et al. Characterization of esterase and alcohol dehydrogenase activity in skin. Metabolism of retinyl palmitate to retinol (Vitamin A) during percutaneous absorption. Pharm. Res. 11, 1155–1159 (1994);

release of vitamin C from a glucoconjugate under the action in this case of a glucosidase activity (patent FR-2 715 565).

Retinoic derivatives are nowadays used in dermatology in various indications, for instance psoriasis or ichthyosis, or alternatively to obtain a depigmentation of the skin (reduction in melanogenesis due to the action of vitamin A); applications to combat ageing of the skin are also sought.

However, the topical use of retinoic derivatives comes up against a certain number of difficulties, due to the lack of stability over time and the lack of stability to light of these derivatives, the irritation resulting from local overconcentrations and also from a poor penetration of these derivatives through the horny layer. This drawback is due to the highly lipophilic nature of the substance which, when deposited on the skin, is in fact largely removed by desquamation. Moreover, side effects (appearance of redness, irritation, oedema and excessive desquamation) limit its use to patients in urgent need, such as those afflicted with persistent acne.

This consequently explains the advantage of the present invention for improving the bioavailability of the active agent in the form of a glucose-spacer-active agent ternary complex, with facilitated penetration and hence the ability to be used in small amount, thus avoiding the harmful effects of local overconcentrations, which are responsible for intolerances.

The present invention relates to a ternary glucosyl complex, which is a bioprecursor of at least one retinoic active principle, in particular retinoic acid, intended for percutaneous application, of formula (I)

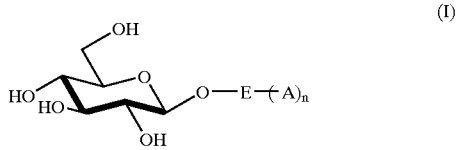

(I)

in which:
E represents a linear, branched or cyclized hydrocarbon-based spacer group of aliphatic or aromatic nature which may contain one or more oxygen hetero atoms and which may bear one or more carbonyl groups,
A represents a residue of a molecule of said retinoic active principle, linked to the spacer group via a carboxylate function,
n=1 or 2.

According to another characteristic of the invention, in the complex of formula I, the group E represents a group which has a complementary pharmaceutical and/or cosmetic activity, in particular which has a moisturizing, depigmenting and/or antibacterial activity.

In particular, the group E can represent a group derived from L or D glycerol, hydroquinone or flavonoids, in particular flavonoids of natural origin.

As specific examples of glucosyl complexes according to the invention, mention will be made of:
para-retinoyl-phenyl-glucopyranoside,
diretinoyl-1,2-propanyl-glucopyranoside,
daidzin retinoate, and
genistin retinoate.

The present invention also covers pharmaceutical or cosmetic compositions for topical use, containing a glucosyl complex as defined above, combined with a vehicle which is suitable for percutaneous administration.

In accordance with the present invention, when said composition is applied to the skin, the complex undergoes an enzymatic double hydrolysis, first of β-glucocerebrosidase type leading to hydrolysis between the glucose and the spacer group, and then of esterase type leading to hydrolysis between the spacer group and the active principle, said active principle thus being released in a delayed manner without an accumulation effect in the various layers of the skin.

Advantageously, the composition according to the invention contains from 0.001% to 10% by weight and preferably from 0.01% to 0.1% by weight of glucosyl complex relative to the total weight of the composition.

The present invention also covers a process for preparing the glucosyl complexes defined above, which is characterized in that a compound of formula II

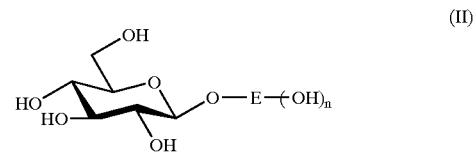

(II)

is reacted with the active principle in acid chloride form.

According to another characteristic of the invention, the compound of formula II corresponds to the more specific formula IIa below

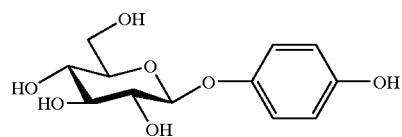

According to another characteristic, the compound of formula II corresponding to formula IIb below

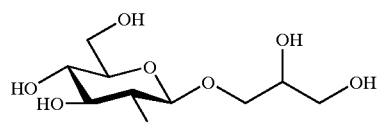

Finally, according to a last characteristic of the invention, the process involves reaction between the compounds of formula II, IIa or IIb with retinoyl chloride.

The glucose-spacer-active agent complex, after rapid migration into the first layers of the epidermis on account of its amphiphilic nature, is recognized as a pseudosubstrate by the two enzymatic activities involved: β-glucocerebrosidase (EC 3.2.1.45) responsible for the hydrolysis between glucose and spacer, and then esterase responsible for the second hydrolysis between spacer and active agent. Needless to say, the spacer may itself be chosen as active agent: this is achieved herein by using hydroquinone as spacer, which is itself active as a depigmenting or antibacterial agent. Two conjugate effects are thus obtained with a single formulation.

It has been demonstrated that the glucoconjugates described in the invention allow a genuine stabilization of retinoic active agents and also very good penetration: whereas derivatives that are too lipophilic, for instance retinoic acid or vitamin E (α-tocopherol), accumulate in the upper layers of the stratum corneum after topical application and are removed by desquamation, their glucoconjugates, on the contrary, included in the same excipient, are partly found (portion not yet hydrolyzed) in the upper layers and also in the lower layers of the stratum corneum, for several days after they have been applied.

The design of these glucoconjugates as pseudosubstrates directed toward the β-glucocerebrosidase activity for the first hydrolysis is justified by several factors:

- this enzyme is accessible from the skin surface, as has been shown by topical application of a specific inhibitor (W. M; Holleran, P. M Elias. J. Lipid. Res. 1994, 35. 905);
- this enzymatic activity which is predominant in the formation of the lipids of the skin surface (40% of the lipids result from this activity) is well conserved firstly between individuals and secondly in the course of the cycle of the seasons;
- under the conditions used in the present invention, this activity is sufficient since it is greater than the esterase activity (example 1).

This enzyme has thus been overexpressed; this has made it possible to determine the kinetic parameters of the substrates relative to a reference. Values are given by way of example for two conjugates, one containing two components and the other containing three components. The values indicate that these pseudosubstrates are better recognized than the reference substrate ($K_M$ values), which is explained by the more lipophilic nature of these conjugates relative to the reference 4-methylumbellifery-glucopyranoside with respect to an enzyme whose substrate is itself highly lipophilic (β-glucosyl-ceramide); moreover, the $V_m$ values show that the active agents are indeed released, with kinetics that are compatible with the intended objective, namely an effect over time starting with a pseudosubstrate applied to the skin in minimal amount but which will be integrally used.

The strategy presented above may be extended and modified in different directions. By way of example:

modification of the spacer:

The spacer may be modified into a structure which is closer to that of the natural substrate (β-glucocerebroside) in which the spacer is related to glycerol. The corresponding glucose-glycerol (L or D)-retinoic acid glucoconjugate has also been synthesized and studied. It should be, noted that the two free hydroxyl groups on the glycerol allow the attachment in ester form of two retinoic units per complex molecule. In this case, the action complementary to the retinoic activity is that of a moisturizing effect provided by in situ release of glycerol;

combination with the retinoic activity of antioxidant properties of flavonoids:

A certain number of flavonoids of natural origin are combined with a saccharide portion which gives them amphiphilic properties.

This is the case, for example, for genistins or daidzin. The absorption of such compounds by the skin surface is thus assured. This first antioxidant activity is combined with the retinoic activity by attachment of one or more retinoic acid molecules per flavone unit. The corresponding structures are given below:

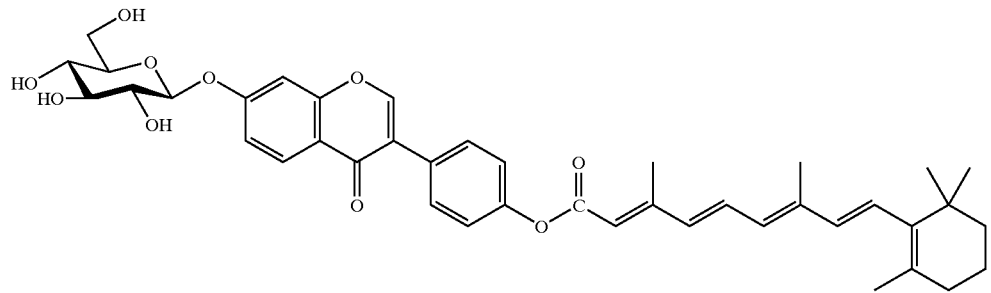

daidzin retinoate

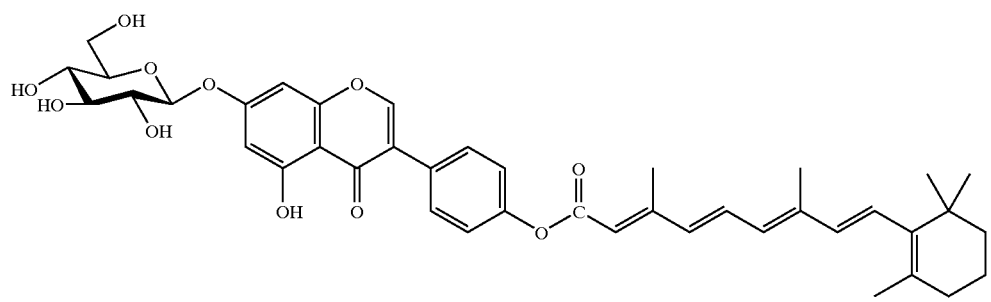

genistin retinoate

In conclusion, the present invention shows the part which may be taken from the β-glucocerebrosidase and esterase activities of the skin surface to obtain the release of various types of active agents from glucosyl bioprecursors.

The structure of the corresponding glucoconjugates ensures good penetration on account of their amphiphilic nature and thus optimal use, very good recognition by the first enzyme, β-glucocerebrosidase, on account of the presence of one or more lipophilic retinyl residues, and a release of the active agents with kinetics which ensure effective cleavage and an effect with remanence over time.

The syntheses of the glucoconjugates, their formulation and their activity as pseudosubstrates are described below:

a) Synthesis of the Bioprecursors

Arbutin retinoate (p-retinoyl-phenyl-glucopyranoside) is prepared from arbutin and retinoyl chloride according to the following reaction scheme.

0.7 g (2.6 mmol) of arbutin is added dropwise to a suspension of 50 mg (2.1 mmol) of sodium hydride in 10 ml of anhydrous DMF cooled to 0° C. and maintained under argon. The 15 ml of the retinoyl chloride solution prepared above are added slowly and the mixture is stirred for one hour while allowing it to warm to room temperature. The excess acid chloride is hydrolyzed with 5 ml of water and the mixture is neutralized by addition of a few drops of saturated sodium hydrogeno carbonate solution. The organic phase extracted, dried and evaporated under vacuum is purified by HPLC (C18: MeOH—$H_2O$: 85-15).

1.1 g of red crystals are obtained. Yield=73%.

$^1$H NMR (CDCl$_3$) δ ppm:

6.9–7.1 (m, 5H, H-2', 3', 5', 6', 11"), 6.1–6.35 (m, 4H, H-7", 8"—CH=CH, 10", 12"—CH=CH), 5.88 (s, 1H, H-14"—CH=CH—), 4.84 (d, 1H, H-1), 3.3–3.9 (m, 6H, H-2, 3, 4, 2 H6), 2.3 (1s, 3H, H-20"—CH$_3$), 1.97–2.03 (1s

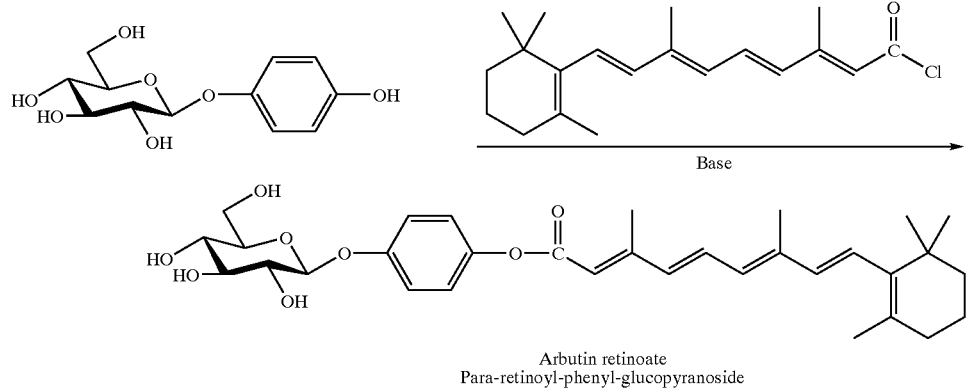

Arbutin retinoate
Para-retinoyl-phenyl-glucopyranoside

This coupling reaction results from a selective and initial dehydrogenation of the phenol function followed by a nucleophilic attack of the phenoxy formed on the acid chloride. The selective dehydrogenation is obtained by the addition, to the maximum, of one equivalent of base (generally 0.9 equivalent) reacting with the phenol group, the pKa value of which (pKa=9) is much lower than that of the other hydroxyl functions of the glucose portion (pKa>16).

Preparation of Retinoyl Chloride 0.41 g (3.3 mmol) of thionyl chloride in methylene chloride (2 ml) is added dropwise to a suspension of 1 g (3.32 mmol) of retinoic acid in 15 ml of anhydrous methylene chloride cooled to 0° C., maintained under argon and containing 0.32 g of pyridine (0.4 mmol). The mixture is allowed to warm to room temperature and stirring is continued for one hour. The red syrup obtained is filtered through glass wool and is immediately used in the following step.

Preparation of arbutin retinoate (p-retinoyl-phenyl-glucopyranoside)

and m, 5H, H-19"—CH$_3$, 4"—CH$_2$), 1.36–1.68 (1m, 1s, 7H, H-2", 3"—(CH$_2$)$_2$, 18"—CH$_3$), 1.02 (1s, 6H, H-16", 17"—Cme$_2$).

$^{13}$C NMR (CDCl$_3$) δ ppm:

166 (C-15"), 155.5 (C-13"), 154.7 (C-1'), 145.6 (C-4'), 140.2 (C-9"), 137.7 (C-6"), 137.4 (C-8"), 135.1 (C-12"), 131.9 (C-11"), 130 (C-5"), 129.7 and 128.9 (C-10", 7"), 122.8 (C-3', 5'), 117.8 (C-14"), 117.4 (C-2', 6'), 100.1 (C-1), 75.7 (C-3), 75 (C-5), 71.5 (C-2), 70.1 (C-4), 61.7 (C-6), 39.6 (C-2"), 34.3 (C-1"), 33.2 (C-4"), 29 (C-16", 17"), 21.8 (C-18"), 19.3 (C-3"), 14.1 and 13 (C-20", 19")

IR: 3418 cm$^{-1}$ OH, 1700 cm$^{-1}$ (ester C=O), 1684, 1576, 1504, 1447, 1358, 1195, 1129 cm$^{-1}$ (CO) MS (m/z) 555 (M$^+$+1), 577 (M$^+$+Na).

With the aim of studying the kinetics of cleavage of arbutin retinoate by β-glucocerebrosidase, we synthesized its hydrolysis product: 4-hydroxyphenyl p-retinoate.

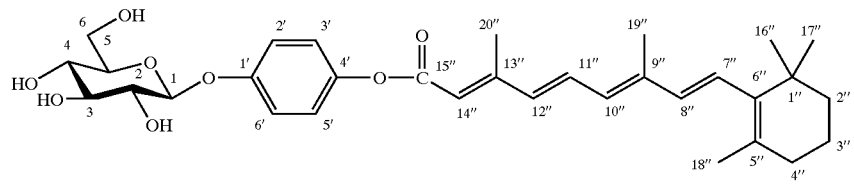

Preparation of Phenol p-retinoate

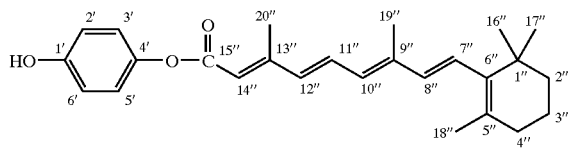

300 mg of dried $Na_2CO_3$ (2.8 mmol) are added to a solution of hydroquinone (300 mg, 2.7 mmol) in anhydrous acetone (15 ml) maintained under argon, followed by slow addition of the 15 ml of retinoyl chloride solution (max 3 mmol) prepared above. After stirring for one hour, the excess acid chloride is hydrolyzed by adding 5 ml of water and the medium is neutralized by adding a few drops of saturated $NaHCO_3$ solution. The organic phase extracted, dried, evaporated under vacuum and purified by HPLC ($C_{18}$: eluant MeOH—$H_2O$: 90-10) gives 0.61 g of red crystals (yield=52%).

$^1$H NMR ($CDCl_3$) δ ppm:
6.95 and 6.78 (2d, 4H, H-2', 3', 5', 6', J-11 Hz), 7.07 (dd, 1H, H-11"), 6.1–6.4 (m, 4H, H-7", 8"—CH=CH, 10", 12"—CH=CH), 5.8 (s, 1H, H-14"—CH=CH—), 2.4 (1s, 3H, H-20"—$CH_3$), 2–2.1 (1s and m, 5H, H-19"—$CH_3$, 4"—$CH_2$), 1.4–1.72 (1m, 1s, 7H, H-2", 3"—$(CH_2)_2$, 18"—$CH_3$), 1.02 (1s, 6H, H-16", 17"—$Cme_2$).

$^{13}$C NMR ($CDCl_3$) δ ppm:
166.4 (C-15"), 155.3 (C-13"), 153.8 (C-1'), 143.9 (C-4'), 140.3 (C-9"), 137.7 (C-6"), 137.4 (C-8"), 135 (C-12"), 131.9 (C-11"), 130.2 (C-5"), 129.5 and 128.9 (C-10", 7"), 122.8 (C-3', 5'), 117.8 (C-14"), 117.3 (C-2', 6'), 39.6 (C-2"), 34.3 (C-1"), 33.2 (C-4"), 29 (C-16", 17"), 21.8 (C-18"), 19.3 (C-3"), 14.2 and 13 (C-20", 19")

MS (FAB/MNBA) m/Z: 415 ($M^+$+Na).

Synthesis of the derivative diretinoyl-1,2-propanyl-glucopyranoside (glucose-glycerol-retinoic acid conjugate)

The figure below describes the reaction scheme we employed to carry out the synthesis of compounds 6 and 7 ($C_2$ enantiomers of the glycerol spacer).

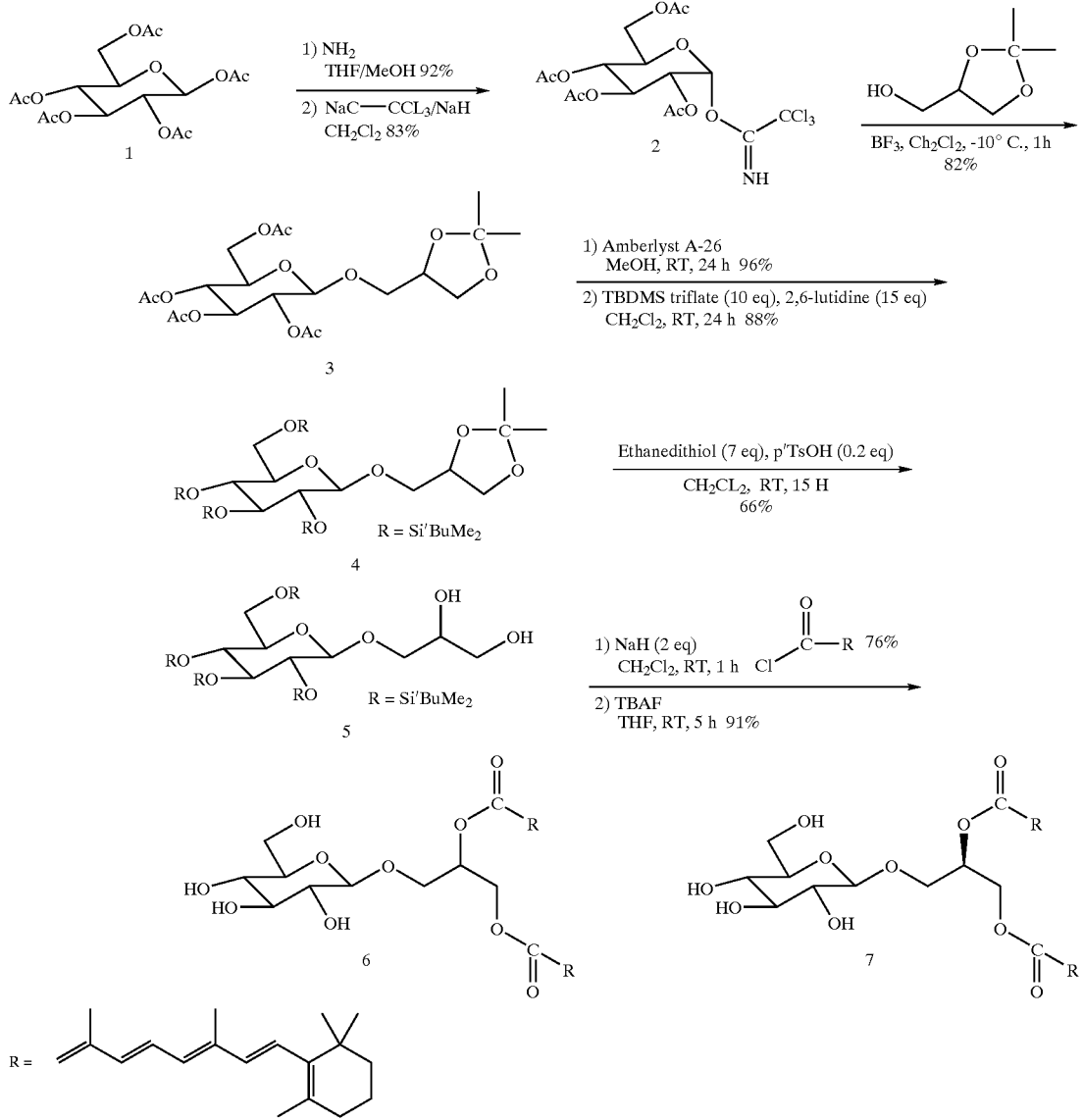

The selective deacylation in position 1 is obtained by aminolysis of the peracetyl glucopyranose 1 using ammonia in the mixture (THF-MeOH: 7-3).

The glucoconjugate 3 was prepared according to the Schmidt method (Schmidt, R. R. Angew. Chem. Int. Ed. Engl. 1986, 25, 212) which allows a stereoselective coupling using the imidate as nucleofugal activator.

This intermediate is synthesized by action of sodium hydride on the glucopyranose deprotected at C-1, which, when converted into an alkoxide, reacts as a nucleophile with trichloroacetonitrile to give the α-imidate 2.

The IR spectrum of this compound shows the characteristic band at 1670 cm$^{-1}$ which may be attributed to the imine bond C=N. The $^1$H NMR spectrum of this compound has a doublet at 6.6 ppm which reflects the presence of the hydrogen at 1 coupled to the hydrogen on carbon C-2, in an α configuration (J=3.5 Hz).

In the presence of Lewis acid (BF3 etherate), the tetraacetyl α-imidate 2 reacts with an alcohol in methylene chloride and leads to the formation of the corresponding glucoconjugate. This reaction results from an initial activation of the imidate function with the Lewis acid, followed by a nucleophilic attack of the alcohol on carbon 1 of the saccharide portion to give the β-glucosyl derivative exclusively (J=8 Hz at C$_1$).

Deprotection of the tetraacetyl glucoconjugates is obtained by treatment with ion-exchange resin (Amberlyst A-26 (OH)) according to a series of ion exchanges at the surface of the resin.

A rapid filtration, after leaving in contact with the resin overnight, allows the deprotected water-soluble compound to be isolated readily in a good yield.

Silylation of the saccharide derivatives with TBDMS triflate generally gives only very poor yields (T. Limori, H. Takashashi and S. Ikegami, Tetrahedron Lett., 1996, 37, 649); we have developed conditions for obtaining a silylation of the 4 free hydroxyl functions of the glucopyranose. The structure of the derivative obtained is established by the $^1$H NMR spectra: the presence of the methyl protons of the TBDMS groups and their integration unequivocally establishes the tetrasilylation.

Selective hydrolysis of the acetal 4 without the concomitant loss of the silyl protections was able to be obtained in a yield of 66% using an excess of ethanedithiol in the presence of a catalytic amount of p-toluenesulfonic acid in methylene chloride. The structure of compound 5 is deduced from the IR spectrum (OH band at 3390 cm$^{-1}$), the mass spectrum (FAB M$^+$+Na=733) and the proton and $^{13}$C NMR spectra which show the disappearance of the methyls of the acetal.

The double esterification is obtained in a yield of 76%, according to the method applied above. Thus, in the presence of two equivalents of sodium hydride, the diol reacts with retinoyl chloride to give the expected diester. The spectral characteristics are in accordance with the proposed structure. The $^1$H and $^{13}$C NMR spectra show the presence of retinoic synthons and tetrasilyl glucose.

The final step of deprotection of the hydroxyl groups borne by the saccharide unit was then performed in anhydrous THF, in the presence of 4 equivalents of TBAF and gave the glucose-glycerol-retinoic acid conjugate 6 in a yield of 90%.

(TBDMS=tert-butyldimethylsilyl; TBAF=tetra-n-butylammonium fluoride))

Preparation of Derivative 3

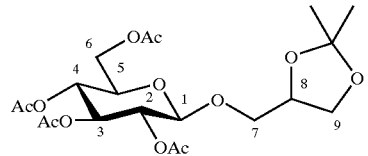

100 mg of BF$_3$ etherate dissolved in 1 ml of CH$_2$Cl$_2$ are added slowly to a mixture, cooled to −10° C., of 1.6 g of imidate (4.6 mmol) and 0.6 g of α,β-isopropylidene-glycerol (4.6 mmol) in 30 ml of CH$_2$Cl$_2$. Stirring is continued for two hours and the mixture is washed with saturated NH$_4$Cl and neutralized with saturated NaHCO$_3$ solution. After drying (MgSO$_4$), the resulting solution is concentrated under reduced pressure and the crude residue is purified by flash chromatography (eluent: hexane-ethyl acetate: 3-2). 1.74 g (3.8 mmol) of white crystals are obtained.

$^1$H NMR CDCl$_3$ δ ppm (300 MHz):
4.36–5.19 (m, 3H, H-1, 2, 3), 4.59 (dd, 1H, H-5), 4.23-3.57 (m, 8H, H-4, 8, 2H6, 2H7, 2H9), 1.96–2.07 (4s, 12H, Ac), 1.39 and 1.32 (2s, 6H, CH$_3$ acetal).

$^{13}$C NMR (CDCl$_3$) δ ppm:
169.3–170.7 (4s, 4 OCOR), 109.4 (C$_{quat}$, isopropylidene), 101 (C-1), 74.2 (C-8), 72.8 (C-3), 71.9 (C-5), 71.2 (C-2), 69.2 (C-7), 68.4 (C-4), 66.8 (C-9), 61.9 (C-6), 26.6 and 25.4 (2CH$_3$ of the acetals).

IR: 1756 cm$^{-1}$ (ester C=O), 1370, 1229, 1167, 1050 cm$^{-1}$ (CO)

Preparation of the Silyl Derivative 4

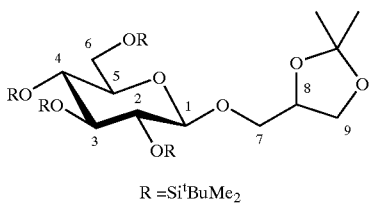

R =Si$^t$BuMe$_2$

A solution of 400 mg (0.86 mmol) of the glucoconjugate 3 in 20 ml of MeOH containing 75 mg of Amberlyst A26 resin is stirred for 24 hours at ambient temperature. The filtered and concentrated solution gives 250 mg of deprotected glucopyranoside derivative (0.85 mmol).

1.8 g (6.8 mmol) of TBDMS triflate are added to a solution of the above deprotected derivative (250 mg) containing 1.1 g of lutidine (10 mmol) in 15 ml of anhydrous methylene chloride, cooled to 0° C. and under argon. The mixture is stirred at ambient temperature for 30 hours. The organic solution washed, dried and evaporated under vacuum gives, after purification by flash chromatography, 0.4 g of colorless resin (eluent: hexane-EtOAc: 30-1).

$^1$H NMR CDCl$_3$ δ ppm (300 MHz):
4.68 (d, 1H, H-1, Jaa=10 Hz), 4.32 (dd, 1H, H-3), 4.05 (t, 1H, H-8), 3.58–3.89 (m, 9H, H-2, 4, 5, 2H6, 2H7, 2H9), 1.35 and 1.41 (2s, 6H, CH$_3$ acetal), 0.85–0.9 (4s, 36H, 4 Si$^t$Bu), 0.04–0.09 (4s, 24H, SiMe$_2$).

$^{13}$C NMR (CDCl$_3$) δ ppm:
109 (C$_{quat}$, isopropylidene), 102.3 (C-1), 82.4 (C-3), 79.1 (C-5), 77.5 (C-2), 74.5 (C-8), 70.2 (C-4), 70.1 (C-7), 67.6 (C-9), 64.2 (C-6), 26.9 and 25.5 (2CH$_3$ of the acetals), 25.9 (CH$_3$ ($^t$Bu)), 17.9–18.4 (4s, C$_{quat}$-Si), −4.11-(−5.4) (4s, CH$_3$Si).

MS (FAB/ONPOE) m/z: 773 (M$^+$+Na)
IR: 1472, 1361, 1255, 1096 cm$^{-1}$ (CO)

Preparation of the Derivative 5

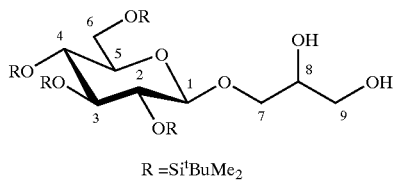

R = Si$^t$BuMe$_2$ 0.88 g of ethanedithiol (9.33 mmol) and 25 mg of p-toluenesulfonic acid (0.132 mmol) are added, under argon and with mechanical stirring, to a solution of 1 g of 4 (1.33 mmol) in 20 ml of methylene chloride. Stirring is continued for a further 15 hours. After washing with saturated NaCl solution, drying (MgSO$_4$) and then filtration, and after concentrating under vacuum, a residue is recovered which is purified by flash chromatography (hexane-ethyl acetate: 1-1). 0.625 g of colorless oil is thus collected (yield=66%).

$^1$H NMR CDCl$_3$ δ ppm (300 MHz):
4.67 (d, 1H, H-1, Jaa=10 Hz), 3.53–3.98 (m, 13H, H-2, 3, 4, 5, 2H6, 2H1', 2H2', 2H3', 2 OH), 0.85–0.9 (4s, 36H, 4 Si$^t$Bu), 0.038–0.09 (4s, 24H, SiMe$_2$).

$^{13}$C NMR (CDCl$_3$) δ ppm:
103.3 (C-1), 82.7 (C-3), 78.9 (C-5), 78.2 (C-2), 72.2 (C-1'), 71 (C-4), 70.2 (C-2'), 64.2 (C-6), 63.9 (C-3'), 25.9 (CH$_3$ ($^t$Bu)), 18.4-17.9 (4s, C$_{quat}$Si), −4.11-(−5.4) (4s, CH$_3$Si).

MS (FAB/ONPOE) m/z: 733 (M$^+$+Na)
IR: 3390 cm$^{-1}$ (OH), 1384, 1218, 1078 cm$^{-1}$ (CO)

Preparation of the Derivative 6(S) or 7(R)

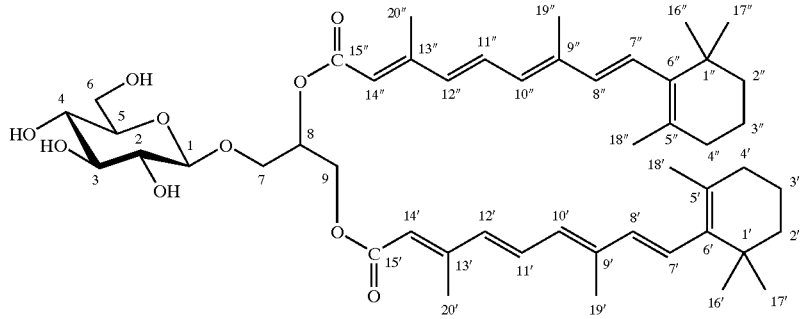

The double esterification is carried out according to the procedure described for the synthesis of arbutin retinoate, but in this case we take methylene chloride as solvent and use 2 equivalents of sodium hydride. The separation of the esterified compound which is in the Rf zone=0.2, eluted with the mixture (hexane-EtOAc: 25-1), is performed by flash chromatography.

The diester obtained (0.68 g, 0.53 mmol) is desilylated with 2.3 g of TBAF (7.4 mmol) in 15 ml of anhydrous THF. After stirring for 4 hours, washing the extract and evaporation to dryness, the product is purified by TLC on silica gel, type 60, in a CH$_2$Cl$_2$—MeOH mixture (95-5), Rf=0.3. 0.4 g of red crystals is isolated.

(6, α$_D$=−8°, S form)
(7, α$_D$=+12°, R form)

$^1$H NMR CDCl$_3$ δ ppm (300 MHz):
6.97 (dd, 2H, H-11', 11"C═CH, JJ=16 Hz), 6.08–6.3 (m, 8H, H-7', 7", 8', 8"—HC═CH, H-10', 10", 12', 12"—C═CH), 5.74 (s, 2H, H-14', 14'—CH═CH,), 4.32–4.37 (m, 2H, H-1.8), 3.23–3.96 (m, 14H, H-2, 3, 4, 5, 2H6, 2H7, 2H9), 2.3 (s, 6H, H-20', 20"—CH$_3$), 1.97–2.03 (1s and m, 10H, H-19', 19"—CH$_3$, H-4', 40"—CH$_2$), 1.36–1.68 (1m, 1s, 14H, H-2', 3', 2", 3"—(CH$_2$)$_2$, H-18', 18"—CH$_3$), 0.94, 0.98, 1, 1.01, (4s, 12H, H-16', 16", 17', 17"—CMe$_2$).

$^{13}$C NMR (CDCl$_3$) δ ppm:
167, 166.5 (C-15', 15"), 154.3, 153.8 (C-13', 13"), 140 (C-9', 9"), 137.7 (C-6', 6"), 137.3 (C-8, 8"), 135.1 (C-12', 12"), 131.6 (C-11', 11"), 130.4 (C-5', 5"), 129.6 and 128.8 (C-10', 10", 7', 7"), 117.9 (C-14', 14"), 103.7 (C-1), 76.1 (C-8), 73.7 (C-3,5), 70 (C-2,4), 68.3 (C-7), 62.5 (C-9), 62 (C-6), 39.6 (C-2', 2"), 34.3 (C-1', 1"), 33.2 (C-4', 4"), 29 (C-16', 16", 17', 17"), 21.8 (C-18', 18"), 19.3 (C-3', 3"), 13.8 and 13 (C-20', 20", 19', 19")

IR: 3427 cm$^{-1}$ OH, 1706 cm$^{-1}$ (ester C═O), 1609, 1457, 1384, 1237, 1141, 1083 cm$^{-1}$ (CO)

MS (FAB/MNBA) m/z: 841 (M$^+$+Na)

b) Formulations

The compositions according to the invention contain from 0.001% to 10% by weight and preferably 0.01% to 0.1% by weight of active precursors relative to the total weight of the composition.

The composition according to the invention may be in the form of an oil-in-water (O/W) or water-in-oil (W/O) emulsion. It may also be in the form of spherules, for instance liposomes, nanocapsules or nanospheres.

When the composition is an emulsion, the proportion of the fatty phase ranges from 5% to 80% by weight and preferably from 5% to 50% by weight relative to the total weight of the composition. The oils, emulsifiers and coemulsifiers used in the composition, in emulsion form, are chosen from those conventionally used in cosmetics. The emulsifier and coemulsifier are present in the composition in a proportion ranging from 0.3% to 10% by weight relative to the total weight of the composition.

The composition according to the invention may also contain acceptable cosmetic or dermatological additives. These additives may be, in particular, antioxidants, bioprecursors of these antioxidants, for instance δ-tocopherylglucopyranoside, surfactants, fatty substances, moisturizers, preserving agents, fragrances, gelling agents, chelating agents, pigments, for instance titanium oxide, screening agents and free vitamins, for instance ascorbic acid.

c) Enzymatic Study

Comparison of the β-glucocerebrosidase and Esterase activities

The stripping technique allows these two different activities to be assayed accurately using the same sample. To do this, we used two artificial substrates, 4-methyl-umbelliferyl-β-D-glucopyranoside (2 mM), to assay the β-glucocerebrosidase activity, and 4-methyl-umbelliferyl-palmitate (2 mM) for that of the esterases.

The following table gives the amount of 4-methyl-umbelliferone released after hydrolysis for one hour by the β-glucocerebrosidase and esterase extracted from three 25 cm$^2$ strips.

It is noted that, at skin pH (pH=5.5), the β-glucocerebrosidase activity is on average twice as high as that of esterase.

|  | β-glucocerebrosidase | Esterase |
| --- | --- | --- |
| Weighted activities Nmol/hour/μg of total proteins | 0.23 ± 0.1 | 0.13 ± 0.08 |

Recognition and hydrolysis of the pseudosubstrates

After confirming that β-glucocerebrosidase is expressed in the keratinocytes, we produced a recombinant enzyme in the baculovirus system. A histidine tail was added to the COOH end of the protein to allow it to be purified by affinity column chromatography.

Thus, we were able to determine the Michaelis constants (Km) and the Vm values of the recombinant β-glucocerebrosidase in particular for the retinoic acid-arbutin glucoconjugate. The kinetics measurements are carried out in a phthalate buffer at pH 5.6 (0.025 M) containing taurocholate (5 mM), purified β-glucocerebrosidase and the test conjugate at various concentrations. The incubation lasts 30 minutes and the amount of hydroquinone-retinoic acid conjugate released is assayed by HPLC. The table below gives the results obtained. It shows, in terms of affinity, that the two test glucoconjugates are much better substrates than the reference. As regards their rates of hydrolysis, these are lower and thus allow effects to be obtained over time.

| Substrates | Km | Vm weighted by the amount of soluble proteins |
| --- | --- | --- |
| 4-Methylumbelli-feryl-glucopyranoside | 2.8 ± 0.7 mM | 4000 ± 1000 nmol/h/mg |
| δ-Tocopheryl-glucopyranoside | 7 ± 1 μM | 453 ± 20 nmol/h/mg |
| Arbutin retinoate | 5 ± 1.2 μM | 235 ± 19 nmol/h/mg |
| Diretinyl-glyceryl-glucopyranoside 7 (R) | 8.6 ± 2.5 μM | 74 ± 7 nmol/h/mg |
| Diretinyl-glycerol-glucopyranoside 7 (S) | 5 ± 0.4 μM | 17 ± 0.4 nmol/h/mg |

What is claimed is:

1. A ternary glucosyl complex, which is a bioprecursor of at least one retinoic active principle, intended for percutaneous application, of formula (I)

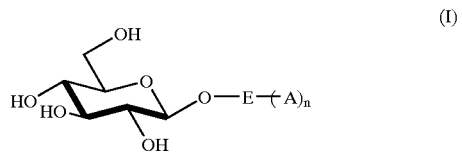

in which:
E represents a cyclic hydrocarbon-based spacer group of aliphatic or aromatic nature which group is optionally substituted by one or more oxygen or hetero atoms and which group may optionally have one or more carbonyl groups attached thereto,
A represents a residue of a molecule of the retinoic active principle, linked to the spacer group via a carboxylate function,
n=1 or 2.

2. The glucosyl complex claim 1, wherein the retinoic active principle is retinoic acid.

3. The glucosyl complex of claim 1, wherein the group E represents a group which has a pharmaceutical and/or cosmetic activity.

4. The glucosyl complex of claim 1, wherein the group E has a moisturizing, depigmenting and/or antibacterial activity.

5. A ternary glucosyl complex, which is a bioprecursor of at least one retinoic active principle, intended for percutaneous application, which is selected from:
para-retinoyl-phenyl-glucopyranoside,
diretinoyl-1,2-propanyl-glucopyranoside,
daidzin retinoate, and
genistin retinoate.

6. A pharmaceutical or cosmetic composition for topical use, which contains a glucosyl complex of claim 1, combined with a vehicle which is suitable for percutaneous administration.

7. The composition of claim 6, which contains from 0.001% to 10% by weight of glucosyl complex relative to the total weight of the composition.

8. The composition of claim 6, which is in the form of an emulsion.

9. The composition of claim 6, which is in the form of spherules.

10. A process for preparing a complex of claim 1, wherein a compound of formula (II)

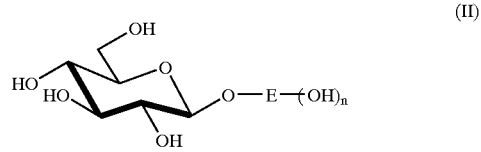

is reacted with the active principle in acid chloride form.

11. The process of claim 10, wherein the compound of formula II corresponds to formula IIa below:

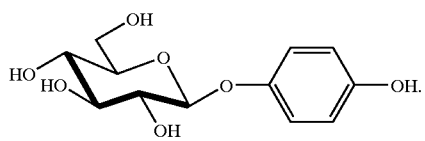

12. The process of claim 10, wherein the compound of formula II corresponds to formula IIb below:

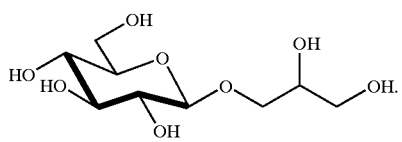

13. The process of claim 10, wherein the acid chloride is retinoyl chloride.

14. The glucosyl complex of claim 1, wherein the group E represents a group derived from flavonoids of natural origin.

15. The composition of claim 7, which contains from 0.01% to 0.1% by weight of glucosyl complex relative to the total weight of the composition.

16. The composition of claim 9, wherein the spherules are selected from liposomes, nanocapsules and nanospheres.

* * * * *

UNITED STATES PATENT AND TRADEMARK OFFICE
CERTIFICATE OF CORRECTION

PATENT NO. : 6,818,657 B1
DATED : November 16, 2004
INVENTOR(S) : Daniel Redoules et al.

It is certified that error appears in the above-identified patent and that said Letters Patent is hereby corrected as shown below:

Column 13,
Line 59, delete "cyclic".
Lines 60-63, delete "which group is optionally substituted by one or more oxygen or hetero atoms and which group may optionally have one or more carbonyl groups attached thereto," and replace with -- selected from the group consisting of moieties derived from L or D glycerol, hydroquinone or flavonoids, --.

Signed and Sealed this

Eleventh Day of October, 2005

JON W. DUDAS
*Director of the United States Patent and Trademark Office*